US009212121B2

(12) United States Patent
Lange et al.

(10) Patent No.: US 9,212,121 B2
(45) Date of Patent: Dec. 15, 2015

(54) PROCESSES FOR PRODUCING TEREPHTHALIC ACID

(71) Applicant: Eastman Chemical Company, Kingsport, TN (US)

(72) Inventors: David Milton Lange, Blountville, TN (US); Ashfaq Shahanawaz Shaikh, Kingsport, TN (US); Patrice L. Riesenberg, Fall Branch, TN (US); Mesfin Ejerssa Janka, Kingsport, TN (US)

(73) Assignee: EASTMAN CHEMICAL COMPANY, Kingsport, TN (US)

( * ) Notice: Subject to any disclaimer, the term of this patent is extended or adjusted under 35 U.S.C. 154(b) by 134 days.

(21) Appl. No.: 14/034,617

(22) Filed: Sep. 24, 2013

(65) Prior Publication Data

US 2015/0087859 A1    Mar. 26, 2015

(51) Int. Cl.
*C07C 51/265*     (2006.01)

(52) U.S. Cl.
CPC .................................. *C07C 51/265* (2013.01)

(58) Field of Classification Search
None
See application file for complete search history.

(56) References Cited

U.S. PATENT DOCUMENTS

| 2,833,816 | A | | 5/1958 | Saffer et al. |
| 3,012,038 | A | | 12/1961 | O'Neill et al. |
| 3,089,906 | A | | 5/1963 | Saffer et al. |
| 3,920,735 | A | | 11/1975 | Wampfler et al. |
| 4,314,073 | A | | 2/1982 | Crooks |
| 4,992,580 | A | | 2/1991 | Partenheimer |
| 5,359,133 | A | | 10/1994 | Nazimok et al. |
| 2006/0205975 | A1 | * | 9/2006 | Lavoie et al. ................. 562/410 |

FOREIGN PATENT DOCUMENTS

| WO | WO 00/37407 A1 | 6/2000 |
| WO | WO 00/66529 A1 | 11/2000 |
| WO | WO 2006/096312 A1 | 9/2006 |
| WO | WO 2006/096313 A1 | 9/2006 |

OTHER PUBLICATIONS

Shaikh, Ashfaq; "TPA Catalyst Enhancement Team Report"; Eastman Research Division, Report # TR-2012-11026, Jan. 25, 2012.

Riesenberg, Patrice L.; "Design of Experiments Results on a TPA Oxidizer May 2010"; Intermediates & Polyester Technology Division, Report #TR-2010-08503, Jul. 20, 2010.
Riesenberg, Patrice L.; "TPA Oxidizer and Digester Optimization Experiments", Worldwide Engineering & Construction, Report #TR-2012-10945, Jan. 6, 2012.
Park, Chang-Man, et al.; "Phthalic Acids and Other Benzenepolycarboxylic Acids"; Kirk-Othmer Encyclopedia of Chemical Technology, vol. 18, 4th ed., (1995), pp. 991-1043.
Bezhanishvili, G. S., et al.; "Improving the Terephthalic Acid Production Process", NTRS "Neftepererabotka i neftekhimiya", 1983, No. 4, pp. 39-40.
Partenheimer, W., et al.; "Methodology and scope of metal/bromide autoxidation of hydrocarbons", Catalysis Today 23, (1995), pp. 65-158.
Partenheimer, W., et al.; "The effect of zirconium in metal/bromide catalysts during the autoxidation of p-xylene Part I. Activation and changes in benzaldehyde intermediate formation"; Journal of Molecular Catalysis A: Chemical 206, (2003), pp. 105-119.
Chester, Arthur W., et al.; "Zirconium Cocatlysis of the Cobalt-Catalyzed Autoxidation of Alkylaromatic Hydrocarbons", Journal of Catalysis, 46, (1977), pp. 308-319.
Steinmetz, G. R., et al.; "The Cobalt/Zirconium-Catalyzed Oxidation of Cyclohexane to Adipic Acid", Journal of Molecular Catalysis, 49, (1988), pp. L39-L42.
New co-pending U.S. Appl. No. 14/034,621, filed Sep. 24, 2013.
Notification of Transmittal of The International Search Report and The Written Opinion of the International Searching Authority, or the Declaration; International Application No. PCT/US2014/055071 with a mailing date of Nov. 28, 2014.
Notification of Transmittal of The International Search Report and The Written Opinion of The International Searching Authority, or the Declaration; International Application No. PCT/US2014/054663 with a mailing date of Dec. 22, 2014.
USPTO Office Action dated Apr. 22, 2015 for copending U.S. Appl. No. 14/034,621.
USPTO Notice of Allowance dated Oct. 8, 2015 for copending U.S. Appl. No. 14/034,621.

* cited by examiner

*Primary Examiner* — Sudhakar Katakam
*Assistant Examiner* — Jennifer C Sawyer
(74) *Attorney, Agent, or Firm* — Steven A. Owen

(57) ABSTRACT

Processes for producing terephthalic acid are disclosed, the processes including a step of combining in a reaction medium para-xylene, a solvent comprising water and a saturated organic acid having from 2-4 carbon atoms, and an oxygen-containing gas, at a temperature for example from about 145° C. to about 175° C., in the presence of a catalyst composition comprising cobalt, manganese, zirconium, and bromine, wherein the zirconium is present in the reaction medium in an amount, for example, from 1 ppm to 50 ppm with respect to the weight of the liquid in the reaction medium.

24 Claims, 1 Drawing Sheet

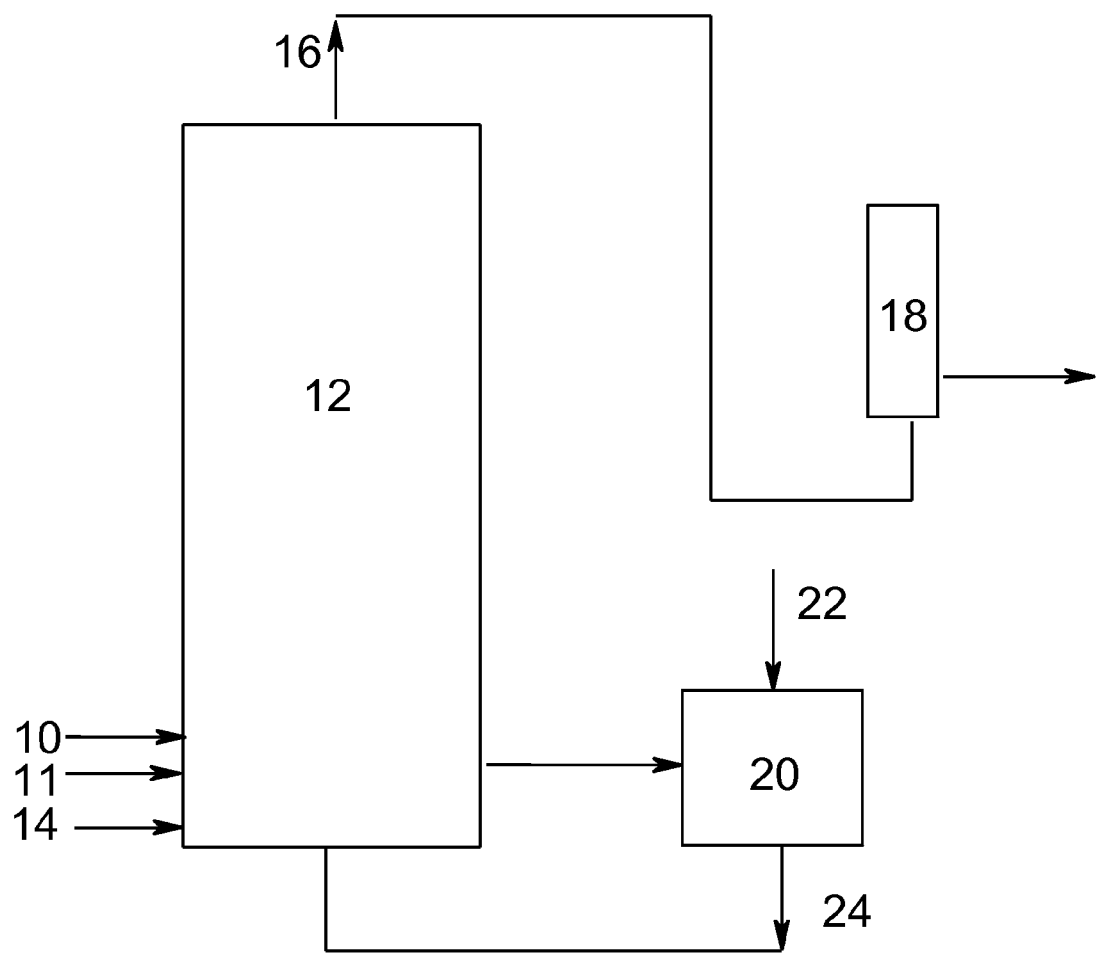

PROCESSES FOR PRODUCING TEREPHTHALIC ACID

FIELD OF THE INVENTION

This invention pertains to improved processes for the production of terephthalic acid by the liquid-phase oxidation of para-xylene, the processes resulting in reduced carbon burn while maintaining product quality.

BACKGROUND OF THE INVENTION

Aromatic dicarboxylic acids such as terephthalic acid and isophthalic acid are used to produce a variety of polyester products, important examples of which are poly(ethylene terephthalate) and its copolymers. These aromatic dicarboxylic acids may be synthesized by the catalytic oxidation of the corresponding dialkyl aromatic compound. For example, terephthalic acid (TPA) and isophthalic acid (IPA) may be produced by the liquid phase oxidation of para-xylene (p-xylene) and meta-xylene (m-xylene), respectively.

These processes typically comprise feeding one or more dialkyl aromatic hydrocarbons, fresh and/or recycled solvent or reaction medium, and catalyst components to a reactor to which a molecular oxygen-containing gas also is fed, typically near the bottom of the reactor. Conventional liquid-phase oxidation reactors are equipped with agitation means for mixing the multi-phase reaction medium. This agitation may be provided, for example, by mechanical agitation means in vessels such as, for example, continuous stirred tank reactors (CSTRs) or in bubble column reactors having relatively high height to diameter ratios. The oxygen-containing process gas rising through the liquid contents of the reactor results in agitation of the reaction mixture. Alternatively, continuous stirred tank reactors may be used, typically having a lower height to diameter ratio than bubble column reactors.

Thus, in one example of such a process, p-xylene is oxidized to produce terephthalic acid. The p-xylene may be continuously or batchwise oxidized in the primary oxidation reactor in the liquid phase, in the presence of an oxygen-containing gas such as air. In such a process, p-xylene, an oxidation catalyst composition, a molecular source of oxygen, and a solvent such as aqueous acetic acid are combined as a reaction medium in the reactor to produce a crude terephthalic acid (CTA) reaction product. Typical oxidation catalyst compositions include a cobalt compound and a manganese compound, usually in combination with a promoter such as a bromine compound. See, for example, U.S. Pat. Nos. 2,833,816, 3,089,906, and 4,314,073, the disclosures of which are incorporated herein by reference. The process conditions are highly corrosive due to the presence of acetic acid and bromine, and titanium lining equipment's are typically used. See, for example, U.S. Pat. No. 3,012,038, incorporated herein by reference. Acetaldehyde may be used as a promoter in place of bromine, in which case reactors and process equipment's made from titanium lining are not necessary. Acetaldehyde is also useful as an initiator. Because the liquid-phase oxidations of dialkyl aromatic compounds just described are highly exothermic reactions, they are commonly carried out in vented reaction vessels, the heat of reaction being removed by vaporization of the process solvent through the upper exit port.

The resulting CTA is not very soluble in the acetic acid solvent under the reaction conditions, and precipitates from the solvent to form a suspension. This crude terephthalic acid suspension includes terephthalic acid solids, a solvent acting as the suspending medium for the solids and containing a small amount of dissolved terephthalic acid; catalyst components; unreacted p-xylene; incompletely oxidized intermediate oxidation products such as para-tolualdehyde (p-TAI), para-toluic acid (p-TA), and 4-carboxybenzaldehyde (4-CBA); and organic impurities such as fluorenones that are known to cause discoloration. The crude terephthalic acid composition is discharged from the oxidation zone and subjected to any of several mother liquor exchange, separation, purification, or recovery methods, with the recovered solvent and catalyst composition being recycled directly back to the oxidation reaction or after processing, such as by catalyst recovery or solvent purification. One such purification technique is hydrogenation using a heterogeneous catalyst. These catalysts are subject to metal poisoning, reducing their activity and requiring more frequent replacement. It is desirable to minimize the amount of incompletely oxidized intermediates and the colored impurities, to reduce these subsequent purification requirements.

Other by-products of the liquid phase oxidation which are partially or completely removed from the reaction mixture in the oxidation reactor are the off-gases, which include water, solvent, unreacted oxygen and other unreacted gases found in the source of the molecular oxygen gas such as nitrogen and carbon dioxide, and additional amounts of carbon dioxide and carbon monoxide that are oxidative losses resulting in part from the catalytic decomposition of the solvent and other oxidizable compounds under the oxidation conditions. The off-gases are vented at the overhead of the oxidation reactor to a distillation column or a condenser to separate the solvent from the other off-gases such as water, carbon dioxide, carbon monoxide, nitrogen, gaseous bromine compounds such as methyl bromide, etc.

Although it is desirable to recover and recycle as much solvent as possible, the solvent is oxidatively decomposed to some extent into its constituent gaseous products, carbon dioxide and carbon monoxide, requiring a fresh source of make-up solvent. This oxidative decomposition is often referred to in the industry as solvent burn, carbon burn, or acid burn, and is generally believed to be responsible in part for the formation of carbon oxides, although a portion of the carbon oxides produced is also the result of oxidative decomposition of the dialkyl aromatics or intermediate reaction products. Controlling or reducing formation of carbon oxides significantly lowers the operating costs of the oxidation process, by allowing a greater amount of solvent to be recovered and recycled back to the oxidation zone, and possibly also by reducing yield loss from the oxidative decomposition of the aromatic reactants. However, a reduction in carbon oxides formation should not come at the expense of significantly reduced yield or conversion, or an increase in the amount of incomplete oxidation products in the crude mixture, and if possible, it would be desirable to simultaneously reduce carbon oxides formation and maintain the conversion. Typically, however, increased conversion is accompanied by an increase in carbon oxides formation.

The activity of a p-xylene oxidation using homogenous catalyst system comprising cobalt, manganese, and bromine can be increased by addition of selected species. Zirconium is known to increase the activity of a terephthalic acid catalyst system to a greater extent than an equivalent addition of cobalt. Past studies focused on the use of Group IV metal addition (such as zirconium) for greater catalyst activity, and levels of zirconium used were typically >100 ppm in the liquid phase and at temperatures as high as 180° C. or more. Further, zirconium appears to be more difficult to remove from the resulting terephthalic acid solids than the other catalyst components, that is, than cobalt, manganese and bromine. Thus, due to the higher levels of zirconium used in prior studies, significant levels of zirconium were typically detected in the resulting terephthalic acid, which had a negative impact on the subsequent hydrogenation catalyst life for processes using hydrogenation purification.

There remains a need in the art for aromatic oxidation processes using cobalt, manganese, bromine, and zirconium that minimize carbon oxides formation by allowing a relatively low reaction temperature while maintaining conversion. These and additional advantages are obtained by the present invention, as further described below.

SUMMARY OF THE INVENTION

The invention relates to processes for producing terephthalic acid, the processes comprising combining in a reaction medium p-xylene, a solvent comprising water and a saturated organic acid having from 2-4 carbon atoms, and an oxygen-containing gas, at a temperature from about 145° C. to about 175° C., in the presence of a catalyst composition comprising cobalt, manganese, zirconium, and bromine, wherein the zirconium is present in the reaction medium in an amount from about 1 ppm to 50 ppm, with respect to the weight of the liquid in the reaction medium.

BRIEF DESCRIPTION OF THE DRAWING

FIG. 1 illustrates a process flow of crude terephthalic acid streams and the overhead of an oxidation unit.

DETAILED DESCRIPTION OF THE INVENTION

The present invention may be understood more readily by reference to the following detailed description of the invention, including the appended FIGURE, and to the examples provided. It is to be understood that the terminology used is for the purpose of describing particular embodiments only and is not intended to be limiting.

As used in the specification and the claims, the singular forms "a," "an," and "the" include plural referents unless the context clearly dictates otherwise. Thus, when the disclosure and the claims use the phrase "a dialkyl aromatic," the phrase is intended to encompass one or more dialkyl aromatics. Similarly, when the phrase "an organic acid having from 2-4 carbon atoms" is used, for example, the phrase is intended to encompass one or more such organic acids.

It is to be understood that the words "comprising" and "containing" are open ended and may include any number and type of unstated steps, processes, or ingredients. The description of method steps does not preclude intervening steps and is not restricted to carrying out the steps in a particular order unless otherwise stated. Numerical ranges include each integer and all fractions thereof between the end points of the stated range.

Unless otherwise indicated, the weight amount of catalyst is based in each instance on the total weight of the liquid in the reaction medium, without regard to the amount of precipitated product in the reaction medium, the amount of which may change during the course of the reaction, especially in those cases in which the process is carried out as a batch or semi-batch process. The defined weight amounts may be determined by removal of a portion of the reaction medium either during or after the reaction, since the amount present in the reaction mixture may differ somewhat from the concentration of catalyst as initially provided to the reaction mixture, due to evaporation, solvent burn, etc.

We have recently determined that a reduction of as little as 2-4° C. of operating temperature in the oxidation of p-xylene to form terephthalic acid significantly reduces solvent oxidation/xylene over-oxidation (carbon burn) and can result in significant operational savings. However, the reduction in temperature with current catalyst levels results in the reduction of conversion (as measured by 4-CBA in the resulting solids) which can impact product quality. Higher levels of cobalt, manganese and bromine could be used to maintain reaction activity at lower temperatures, but would result in higher levels of catalyst in the final product. Hence, to realize these savings while not compromising the product quality (as measured by 4-CBA and catalyst content in the final product), there is a need to maintain conversion at lower reaction temperatures to reduce carbon burn resulting in a lower operational cost.

Because of the need just described, the effect of adding small amounts of zirconium (<50 ppm) was assessed in the laboratory. Surprisingly, it was found that the addition of smaller amounts of zirconium were found to significantly increase reaction activity in the 150° C. to 170° C. reaction temperature range. Thus, it was found that adding a small amount of zirconium (typically <50 ppm in oxidizer liquid phase) enables a reduction in temperature that reduces carbon burn resulting in significant savings while maintaining product quality, as measured by 4-CBA and catalyst levels. Further, because of the small amounts of zirconium used, the resulting levels of zirconium incorporation in the final product are typically below detection limits, minimizing the effect on subsequent purifications such as hydrogenation.

According to the invention, the extent of carbon oxides formation, in part a result of oxidative loss of solvent, observed in the oxidation of p-xylene to terephthalic acid, is minimized by the use of moderate reaction temperatures. We have discovered that the use of catalyst compositions according to the invention, at moderate reaction temperatures, improves the conversion with a concomitant decrease in impurities generation rate, such as that for benzoic acid, which in turn is a good indicator of other undesirable impurities. The use of the catalyst compositions according to the invention also leads to low quantities of CO and $CO_2$ produced in the course of the reaction, which is believed to be a good indicator of the extent of acid burn. Such a decrease in carbon oxides formation in the oxidation of p-xylene translates into significant cost savings in the manufacture of terephthalic acid, by reducing for example the extent of acid burn.

Thus, according to the invention, p-xylene, provided as a liquid, is oxidized in an aqueous aliphatic solvent, such as acetic acid and water, with oxygen-containing gas, in the presence of a catalyst system comprising cobalt atoms, manganese atoms, zirconium atoms, and bromine atoms, wherein the zirconium is present in the reaction medium in an amount, for example, from 1 ppm to 50 ppm with respect to the weight of the liquid in the reaction medium. The processes may be carried out at temperatures, for example, from about 145° C. to about 175° C., or from about 150° C. to about 170° C., or from 155° C. to 165° C. Alternatively, the processes may be carried out at a temperature of at least 125° C., or at least 130° C., or at least 135° C., or at least 140° C., and up to about 145° C., or up to about 150° C., or up to about 155° C., or up to about 160° C.

According to the invention, the zirconium atoms in the reaction medium may be present in an amount, for example, of at least about 1 ppm, or at least 2 ppm, or at least 3 ppm, or at least 5, 7, or 9 ppm, up to about 50 ppm, or up to about 45 ppm, or up to about 42 ppm. The processes according to the invention produce terephthalic acid, with good conversions, in those embodiments in which p-xylene is the reactant, a concentration of 4-carboxybenzaldehyde (4CBA), based on the weight of terephthalic acid produced, of less than 6 wt. %, or less than 5 wt. %, or less than 3 wt. %, or less than 1 wt. %, while obtaining reduced carbon oxides formation, for example no more than about 1.2 moles $CO_X$, or no more than about 0.6 mole $CO_X$, or no more than about 0.3 mole $CO_X$, in each case with respect to the molar quantity of para-xylene compound fed to the reactor. In one example, the process produces no more than about 1.2 moles $CO_X$ per mole of para-xylene provided to the reaction medium.

Thus, in one embodiment, the process comprises oxidizing p-xylene in the liquid phase. The liquid phase may at any moment comprise any or all of: the feed reactants, p-xylene, the oxygen-containing gas, the solvent, the catalyst composition, and the dicarboxylic acid reaction product dissolved or suspended in the reaction mixture, especially when the process is carried out as a continuous process. The products of the processes according to this embodiment include the terephthalic acid solids as the predominant product (for example, at least 50 wt. % of the solids), and incomplete oxidation products which may be found in the solids, in the liquid phase, or in both. The p-xylene fed to the oxidation reactor may be purified of contaminants which may interfere with the oxidation reaction. The reactant feed may be pure or a mix of the compound isomers or lower or higher homologues, as well as some saturated alicyclic or aliphatic compounds having similar boiling points to the aromatic or fused ring compounds. However, in this embodiment, at least 80 wt. %, or at least 95 wt. %, or at least 98 wt. % of the liquid reactants is the p-xylene reactant.

According to the invention, the liquid phase oxidation processes are carried out in the presence of an aliphatic solvent. Suitable solvents are those which are solvents for the dialkyl aromatics under the oxidation reaction conditions, and especially those in which the dicarboxylic acid products form a pumpable crude flow discharged from the oxidation reactor. Suitable solvents include mixtures of water and the aliphatic solvents. In one example, the aliphatic solvents are aliphatic carboxylic acids, and include aqueous solutions of $C_2$ to $C_6$ monocarboxylic acids, and in one embodiment has $C_2$ to $C_4$ monocarboxylic acids, e.g., acetic acid, propionic acid, n-butyric acid, isobutyric acid, n-valeric acid, trimethylacetic acid, caprioic acid, and mixtures thereof. In one embodiment, the saturated organic acid comprises acetic acid. In another embodiment, the solvent is volatile under the oxidation reaction conditions to allow it to be taken as an off-gas from the oxidation reactor. It is found in some examples that the solvent selected is one in which the catalyst composition is soluble under the reaction conditions.

In one embodiment, the solvent is an aqueous acetic acid solution, having a concentration, for example, from about 90 to about 97 wt. % acetic acid, based on the weight of the liquid phase of the reaction medium. In various embodiments, the solvent comprises a mixture of water and acetic acid which, for example, has a water content sufficient to provide at least about 3.0% by weight water in the reaction medium, or at least 4.0 wt. %, or from about 3.0 wt. % to about 15 wt. %, or from 3.0 wt. % to 11 wt. %.

The crude dicarboxylic acid composition may be discharged from the oxidation zone and subjected to a variety of mother liquor exchange, separation, purification, or recovery methods. These methods can provide recovered solvent and catalyst composition for recycling back to the oxidation zone.

Thus, a portion of the solvent feed to the primary oxidation reactor may be obtained from a recycle stream obtained by displacing, for example, from about 80 to 90% of the mother liquor taken from the crude reaction mixture stream discharged from the primary oxidation reactor with fresh, wet acetic acid. This exchange may be accomplished in any convenient apparatus but can most easily be accomplished in a centrifuging apparatus, such as one or more cyclones.

The processes according to the invention are conducted in the presence of a source of oxygen. This may be accomplished by feeding an oxygen-containing gas to the oxidation reactor to allow the gas to contact the liquid reaction mixture in the reactor. The predominately gas-phase oxidant stream introduced into the reactor comprises molecular oxygen ($O_2$), for example in the range from about 5 to about 100 mole percent molecular oxygen, or from about 10 to about 50 mole percent molecular oxygen, or from 15 to 25 mole percent molecular oxygen. The balance of the oxidant stream typically is comprised primarily of a gas or gases, such as nitrogen, that are inert to oxidation. Thus, the oxidant stream may comprise dry air containing about 21 mole percent molecular oxygen and substantial amounts of nitrogen. In one embodiment, the oxygen-containing gas comprises air.

The presence or absence of carbon dioxide in the oxidant stream is not seen to be especially critical, and may thus vary within a broad range, from substantially no carbon dioxide, to that amount of carbon dioxide normally found in fresh air (about 0.05 wt. %), or up to about 1 wt. %, or up to 2 wt. %, or up to 4 wt. %, or even greater amounts.

In the processes according to the invention, the oxidation reaction proceeds at elevated temperatures and pressures, so that at least a portion of the reaction mixture is in the liquid phase. During oxidation, the time-averaged and volume-averaged temperature of the reaction medium may be maintained, for example, in the range from about 145° C. to about 175° C., or from about 150° C. to about 170° C., or from 155° C. to 165° C. The overhead pressure above the reaction medium may, for example, be maintained in the range of from about 1 to about 40 bar gauge (barg), or from about 2 to about 20 barg, or from 2 to 8 barg.

We have found according to the invention that relatively moderate oxidation temperatures may help to reduce the extent of carbon oxides formation, believed to represent in part the extent of solvent burn. The processes of the invention thus are particularly well suited for oxidizing p-xylene at relatively moderate temperatures, as already described, although higher temperatures may be desired to improve reaction rate.

The catalyst compositions employed in the processes of the invention comprise cobalt atoms, manganese atoms, zirconium atoms, and bromine atoms, supplied by any suitable means, as further described below. In one embodiment, the catalyst compositions consist of cobalt atoms, manganese atoms, zirconium atoms, and bromine atoms. The catalyst composition is typically soluble in the solvent under reaction conditions, or it is soluble in the reactants fed to the oxidation zone. In one example, the catalyst composition is soluble in the solvent at 40° C. and 1 atm, and is soluble in the solvent under the reaction conditions.

The cobalt atoms may be provided, for example, in an amount of at least 500 ppm, or at least 750 ppm, or at least 1,000 ppm, or from about 500 ppm to about 6,000 ppm, or from 750 ppm to 4,500 ppm, or from 1,000 ppm to 4,000 ppm, in each instance with respect to the weight of the liquid in the reaction medium. The cobalt atoms may be provided in ionic form as inorganic cobalt salts, such as cobalt bromide, cobalt nitrate, or cobalt chloride, or organic cobalt compounds such as cobalt salts of aliphatic or aromatic acids having 2-22 carbon atoms, including cobalt acetate, cobalt octanoate, cobalt benzoate, cobalt acetylacetonate, and cobalt naphthalate.

The weight amounts of each of cobalt, manganese, zirconium, and bromine are based on the atomic weight of the atoms, whether or not the atoms are in elemental form or in ionic form. For example, the amount of cobalt refers to the amount of cobalt atoms, whether elemental or ionic, and not the amount of cobalt acetate. The stated concentrations of catalyst components are based on the quantity of catalyst components in the liquid portion of the reaction medium in the oxidation reactor. The catalyst component concentrations may be measured, for example, by sampling the oxidation reactor.

The oxidation state of cobalt when added as a compound to the reaction mixture is not limited, and includes both the +2 and +3 oxidation states.

The manganese atoms may be provided as one or more inorganic manganese salts, such as manganese borates, manganese halides, manganese nitrates, or organometallic manganese compounds such as the manganese salts of lower aliphatic carboxylic acids, including manganese acetate, and manganese salts of beta-diketonates, including manganese acetylacetonate. Manganese of the catalyst composition may be provided in an amount from about 20 ppm to about 425 ppm, or from 20 ppm to about 300 ppm, or from about 20 ppm to about 200 ppm, with respect to the weight of the liquid in the reaction medium.

The zirconium may be provided as zirconium oxide or as one or more inorganic zirconium salts, such as zirconium chloride, zirconium bromide, and zirconium sulfate, or organometallic zirconium compounds such as zirconium acetate, zirconium acetate hydroxide, zirconium acetylacetonate, zirconium butoxide, zirconium propoxide or zirconyl acetate. In one embodiment, the zirconium is provided as one or more of: zirconium oxide, zirconium bromide, zirconium chloride, zirconium acetate, zirconium acetate hydroxide, zirconium acetylacetonate, zirconium hydroxide, zirconium butoxide, zirconium propoxide, or zirconyl acetate. In another embodiment, the zirconium is provided as zirconium acetate, zirconium acetate hydroxide, or zirconyl acetate.

The zirconium atoms of the catalyst composition may thus be present in an amount of at least 0.5 ppm, or at least 1 ppm, or at least 2 ppm, or up to about 50 ppm, or up to about 40 ppm or up to about 30 ppm, or up to about 25 ppm. Suitable ranges of zirconium in the reaction medium may thus vary from about 0.5 ppm to 50 ppm, or from about 1 ppm to about 25 ppm, or from about 25 ppm to 50 ppm. In one embodiment, the zirconium is present in the reaction medium in an amount from about 2 ppm to about 45 ppm. In another embodiment, the zirconium is present in the reaction medium in an amount from about 3 ppm to about 40 ppm. In another embodiment, the zirconium is present in the reaction medium in an amount from about 5 ppm to about 35 ppm. In yet another embodiment, the zirconium is present in the reaction medium in an amount of about 25 ppm, or about 20 ppm to about 30 ppm, or about 15 ppm to about 35 ppm, or about 10 ppm to about 40 ppm.

The bromine component may be added as elemental bromine, in combined form, or as an anion. Suitable sources of bromine include but are not limited to hydrobromic acid, sodium bromide, ammonium bromide, potassium bromide, tetrabromoethane, benzyl bromide, alpha-bromo-p-toluic acid, and bromoacetic acid. Hydrobromic acid, sodium bromide, or alpha-bromo-p-toluic acid may be preferred bromine sources. Bromine is provided in an amount from about 750 ppm to about 6,000 ppm, or from about 900 ppm to about 5000 ppm, or from about 1000 ppm to about 4500 ppm, each with respect to the total weight of liquid in the reaction medium.

According to the invention, the relative amounts of elements in the catalyst composition are selected so as to achieve acceptable conversion, while limiting acid burn. Thus, the weight ratio of cobalt atoms to bromine atoms may be, for example, from about 0.6 to about 10, or from 0.7 to 8, or from 0.8 to 5. In one embodiment, the weight ratio of cobalt to bromine is from about 0.6 to about 10. In another embodiment, the weight ratio of cobalt to bromine is from about 0.7 to about 8. In another embodiment, the weight ratio of cobalt to bromine is from about 0.8 to about 5.

In an important aspect of the invention, the ratio of cobalt atoms to manganese atoms may be from about 10.0 to about 400, or from about 12 to about 300, or from about 15 to about 250. In various other embodiments, the ratio of cobalt atoms to manganese atoms will be at least about 10, or at least 12, or at least 15, or at least 18, up to about 150, or up to about 200, or up to about 300, or up to about 400. In one embodiment, the weight ratio of cobalt to manganese in the reaction mixture is from about 15 to about 250.

Other organic or non-metallic catalyst components can be included in the catalyst composition of the invention, or the processes may be carried out in the substantial absence of additional organic or non-metallic catalysts. For example, the catalyst composition may include a source of pyridine. The pyridine component of the catalyst composition may be added to a primary oxidation reactor or to post oxidation reactors. The pyridine component can be in the form of pyridine per se or in the form of a compound of pyridine.

Further, the processes according to the invention may be carried out in the presence of, or in the substantial absence of, one or more aldehydes or ketones.

Further, the processes according to the invention may be carried out in the presence of additional metal atoms, or in the substantial absence thereof, so long as the catalyst composition comprises cobalt atoms, manganese atoms, and zirconium atoms, with bromine atoms provided as a promoter. Such additional metals may include, but not be limited to, molybdenum, sodium, potassium, copper, hafnium, chromium, cerium, iron, tungsten, bismuth, vanadium, and palladium. In one embodiment, the total amount of zirconium, nickel, chromium, and cerium is no more than 50 ppm.

The catalyst composition can be formed by adding each source to the oxidation reactor separately, in sequence, or simultaneously, or a prepared composition may be added to the oxidation reactor and in either case, the addition may be made as an initial batch or continuously during the course of the oxidation reaction. The catalyst composition prepared as a batch may be dissolved in the solvent to form a catalyst feed followed by adding the catalyst feed to the primary oxidation reactor. Each component, or the catalyst composition batch, can be added to the primary oxidation reactor before, during, or after addition of the solvent. In a continuous process, the catalyst components or the catalyst composition may be added simultaneously with the solvent feed, or in the solvent feed, or separately metered as required for fresh make-up.

After the initial charge of catalyst composition in a continuous process, the residual mother liquor from the primary oxidation may supply a portion of the necessary catalyst components to the primary oxidation reactor by partial displacement of the primary oxidation mother liquor with fresh solvent. The remainder can be made up with a continuous fresh feed of make-up catalyst.

In the processes according to the invention, the extent of solvent burned and rendered unusable as a recycle stream may be reduced relative to typical processes. While the absolute amount of solvent burn in the present invention may be reduced, this reduction is not achieved at the expense of acceptable conversion. Obtaining a low amount of carbon oxides formation might be achieved by running the reaction at low oxidation temperatures or using a less active catalyst, but this typically results in lowered conversion and increased quantities of intermediates. The processes of the invention have the advantage of maintaining a low carbon oxides formation while minimizing the impact on conversion.

Thus, in one embodiment, the amount of carbon oxides formation (in total moles of CO and $CO_2$, expressed as COx per mole of dialkyl aromatic compounds fed to the reactor) is no more than about 1.2 moles COx/mole, or no more than about 0.6, or no more than about 0.3 mole $CO_x$ per mole of dialkyl aromatic compounds fed to the reactor.

Thus, in a process in accordance with the present invention, p-xylene, in an amount, for example, from about 2 to about 15 wt. %, based on the weight of liquid in the reaction medium, is combined with acetic acid, and an oxygen-containing gas, at a temperature from about 125° C. to about 155° C., or from about 145° C. to about 175° C., using a catalyst composition comprising cobalt atoms, manganese atoms, and zirconium atoms, with bromine atoms provided as a promoter, wherein the weight ratio of cobalt to manganese may be, for example, from about 10 to about 400, and wherein the zirconium atoms are present in amounts as already described.

An embodiment of the invention will now be described referring to the accompanying FIG. 1, in which p-xylene is introduced via conduit 10 into primary oxidation reactor 12, and aqueous acetic acid solvent having dissolved therein the catalyst composition of the invention fed through line 11 to the reactor 12. If desired, the p-xylene, solvent, and catalyst composition charges may be fed to reactor 12 at a plurality of points, or fed together through one line. An oxygen-containing gas under pressure is introduced near the bottom of the reactor 12 via conduit 14. The preferred oxygen-containing gas is air or oxygen-enriched air. The flow rate of the oxygen-containing gas to reactor 12 is controlled to maintain between about 2 and 9 volume percent oxygen (calculated on a dry, solvent free basis) in the off-gas which exits the reactor via conduit 16. The reactants in reactor 12 are maintained at an elevated pressure of about 50 to 175 psia to maintain a contained, volatizable reaction medium substantially in the liquid state at the reaction temperature, for example, of about 125° C. to about 155° C., or from about 145° C. to about 175° C.

During the course of the oxidation reaction, exothermic heat of reaction and water generated by the oxidation of p-xylene are removed from reactor 12 by vaporization of a portion of the liquid reaction medium. These vapors, known as reactor off-gas, comprise vaporized acetic acid solvent, about 5 to 30 weight percent water, and oxygen-depleted process gas containing minor amounts of decomposition products including catalyst residue, as well as additional carbon dioxide and carbon monoxide generated by the decomposition of acetic acid. The reactor off-gas passes upwardly through the reactor 12 and is conveyed via conduit 16 to the lower portion of water removal column 18 for distillation and recovery of the acetic acid back to the primary oxidation reactor. The crude reaction mixture is discharged from the primary oxidation reactor to a solid/liquid separator 20 into which is fed fresh acetic acid through line 22 to exchange the mother liquor discharged through line 24. The mother liquor containing acetic acid and the catalyst composition is subjected to conventional purification and purging techniques to recover and recycle the catalyst composition to the primary oxidation reactor 12.

Suitable dialkyl aromatic compounds useful as reactor feed-mixture components or ingredients in the methods of the present invention include dialkyl benzenes and naphthalenes such as o-xylene, m-xylene, p-xylene, 2,6-dimethylnaphthalene, 2,7-dimethylnaphthalene and 2,6-diisopropylnaphthalene. The respective aromatic carboxylic acid products of these alkyl aromatic compounds are orthophthalic acid, isophthalic acid, terephthalic acid (TPA), and 2,6- and 2,7-naphthalenedicarboxylic acids. The processes of the invention can be used to produce TPA and isophthalic acid, and are particularly well suited for the production of benzenedicarboxylic and naphthalenedicarboxylic acids, especially TPA.

Suitable aqueous aliphatic acid solvents useful in the methods of the invention are those that are readily volatilizable at the reaction temperatures. Among such solvents are aqueous solutions of $C_2$ to $C_6$ monocarboxylic acids, e.g., acetic acid, propionic acid, n-butyric acid, isobutyric acid, n-valeric acid, trimethylacetic acid, caprioic acid, and mixtures thereof. In one embodiment, the volatilizable monocarboxylic aliphatic acid solvent is an aqueous acetic acid solution.

Further description of the oxidation of alkyl aromatics to benzenepolycarboxylic acids may be found in the "Phthalic Acids and Other Benzenepolycarboxylic Acids" entry of Kirk-Othmer *Encyclopedia of Chemical Technology*, Vol 18, 4th ed., (1995) pp. 991-1043, the relevant portions of which are incorporated herein by reference.

The 4-carboxybenzaldehyde (4CBA) is an incomplete oxidation product of the p-xylene oxidation to TPA. The presence of 4CBA in the product mixture can indicate the degree of conversion while lower 4CBA levels may indicate higher conversion of p-xylene.

As described above some acetic acid solvent decomposes to produce mainly carbon dioxide, carbon monoxide, and methyl acetate. The total oxidative decomposition products can be estimated in the examples by measuring the number of moles of carbon dioxide and carbon monoxide exiting in the oxidizer vent gas. To achieve satisfactory results for the oxidation process, the amount of carbon oxides formation should be minimal while the rate of p-xylene conversion to TPA is maximized. Thus, the amount of 4CBA found in the oxidizer filtrate is a measure of the rate of the oxidation, and the amount of carbon oxides in the vent gas is a measure of reaction efficiency and the related cost of the oxidation process.

LIST OF NON-LIMITING EMBODIMENTS

Embodiment A is a process for producing terephthalic acid, the process comprising combining in a reaction medium paraxylene, a solvent comprising water and a saturated organic acid having from 2-4 carbon atoms, and an oxygen-containing gas, at a temperature from about 145° C. to about 175° C., in the presence of a catalyst composition comprising cobalt, manganese, zirconium, and bromine, wherein the zirconium is present in the reaction medium in an amount from about 1 ppm to 50 ppm, with respect to the weight of the liquid in the reaction medium.

The process of Embodiment A wherein the zirconium is present in the reaction medium in an amount from about 2 ppm to about 45 ppm.

The process of Embodiment A or Embodiment A with one or more of the intervening features wherein the zirconium is present in the reaction medium in an amount from about 3 ppm to about 40 ppm.

The process of Embodiment A or Embodiment A with one or more of the intervening features wherein the zirconium is present in the reaction medium in an amount from about 5 ppm to about 35 ppm.

The process of Embodiment A or Embodiment A with one or more of the intervening features wherein the total amount of zirconium, nickel, chromium, and cerium is no more than 50 ppm.

The process of Embodiment A or Embodiment A with one or more of the intervening features wherein the weight ratio of cobalt to manganese in the reaction mixture is from about 15 to about 250.

The process of Embodiment A or Embodiment A with one or more of the intervening features wherein the saturated organic acid comprises acetic acid.

The process of Embodiment A or Embodiment A with one or more of the intervening features which further comprises a process wherein the temperature is from about 150° C. to about 170° C.

The process of Embodiment A or Embodiment A with one or more of the intervening features wherein the temperature is from about 155° C. to about 165° C.

The process of Embodiment A or Embodiment A with one or more of the intervening features wherein the zirconium is provided as one or more of: zirconium oxide, zirconium bromide, zirconium chloride, zirconium acetate, zirconium acetate hydroxide, zirconium acetylacetonate, zirconium hydroxide, zirconium butoxide, zirconium propoxide, or zirconyl acetate.

The process of Embodiment A or Embodiment A with one or more of the intervening features wherein the zirconium is provided as zirconium acetate, zirconium acetate hydroxide, or zirconyl acetate.

The process of Embodiment A or Embodiment A with one or more of the intervening features wherein the oxygen-containing gas comprises air.

The process of Embodiment A or Embodiment A with one or more of the intervening features wherein the cobalt is provided in an amount from about 500 ppm to about 6,000 ppm, with respect to the weight of liquid in the reaction medium.

The process of Embodiment A or Embodiment A with one or more of the intervening features wherein the cobalt is provided in an amount from about 750 ppm to about 4,500 ppm, with respect to the weight of liquid in the reaction medium.

The process of Embodiment A or Embodiment A with one or more of the intervening features wherein the cobalt is provided in an amount from about 1,000 ppm to about 4,000 ppm, with respect to the weight of liquid in the reaction medium.

The process of Embodiment A or Embodiment A with one or more of the intervening features wherein the manganese is provided in an amount from about 20 ppm to about 425 ppm, with respect to the weight of liquid in the reaction medium.

The process of Embodiment A or Embodiment A with one or more of the intervening features wherein the manganese is provided in an amount from about 20 ppm to about 300 ppm, with respect to the weight of liquid in the reaction medium.

The process of Embodiment A or Embodiment A with one or more of the intervening features wherein the manganese is provided in an amount from about 20 ppm to about 200 ppm, with respect to the weight of liquid in the reaction medium.

The process of Embodiment A or Embodiment A with one or more of the intervening features wherein the bromine is provided in an amount from about 750 ppm to about 6,000 ppm, with respect to the weight of liquid in the reaction medium.

The process of Embodiment A or Embodiment A with one or more of the intervening features wherein the bromine is provided in an amount from about 900 ppm to about 5,000 ppm, with respect to the weight of liquid in the reaction medium.

The process of Embodiment A or Embodiment A with one or more of the intervening features wherein the bromine is provided in an amount from about 1,000 ppm to about 4,500 ppm, with respect to the weight of liquid in the reaction medium.

The process of Embodiment A or Embodiment A with one or more of the intervening features wherein the weight ratio of cobalt to bromine is from about 0.6 to about 10.

The process of Embodiment A or Embodiment A with one or more of the intervening features wherein the weight ratio of cobalt to bromine is from about 0.7 to about 8.

The process of Embodiment A or Embodiment A with one or more of the intervening features wherein the weight ratio of cobalt to bromine is from about 0.8 to about 5.

The process of Embodiment A or Embodiment A with one or more of the intervening features wherein the process produces no more than about 1.2 moles $CO_X$ per mole of para-xylene provided to the reaction medium.

EXAMPLES

General

The cobalt(II) acetate hydrate, manganese(II) acetate hydrate, zirconium acetate hydroxide, hydrobromic acid, and sodium bromide were purchased from commercial suppliers and used as received. The para-xylene (p-xylene), solvents, and peracetic were also purchased from commercial suppliers and used as received.

Liquid Chromatography Measurements

Samples are analyzed with an Agilent 1200 series LC unit consisting of a quaternary pump, an autosampler (5 uL injection), a thermostated column compartment (30° C.) and a diode array UV/vis detector (240 nm). The chromatograph is fitted with two (2) 150 mm×4.6 mm Waters Spherisorb ODS2 columns (3 micron particles) in series. The solvent flow program is shown in Table 1 below: Channel A is 0.1% phosphoric acid in water, channel B is acetonitrile, and channel C is tetrahydrofuran (THF).

TABLE 1

LC Solvent Flow Program

| Time (min) | % A | % B | % C | Flow (mL/min) |
|---|---|---|---|---|
| 0 | 79.0 | 0.0 | 21.0 | 0.90 |
| 20 | 79.0 | 0.0 | 21.0 | 0.90 |
| 38 | 34.0 | 45.0 | 21.0 | 1.00 |
| 38.5 | 14.0 | 65.0 | 21.0 | 1.00 |
| 39.5 | 14.0 | 65.0 | 21.0 | 1.00 |
| 40 | 79.0 | 0.0 | 21.0 | 1.10 |
| 41 | 79.0 | 0.0 | 21.0 | 1.30 |
| 44 | 79.0 | 0.0 | 21.0 | 0.90 |
| 46 | 79.0 | 0.0 | 21.0 | 0.90 |

EZChrom elite is used for control of the HPLC and for data processing. A 3 point linear calibration is used for the quantification of 4-CBA. Samples are prepared by dissolving ~0.20 g of TPA solid or 0.10 g of TPA filtrate (weighed accurately to 0.0001 g) in 10 ml of 50:50 DMF/THF. Sonication is used to ensure complete dissolution of the sample in the solvent. A portion of the prepared sample is transferred to an autosampler vial for injection onto the LC.

Inductively Coupled Plasma (ICP) Analysis

Crude terephthalic acid samples were digested using sulfuric acid with nitric acid added drop wise as an oxidizing agent. The samples were then cooled and diluted to the desired volume and analyzed using a Perkin Elmer ICP-OES instrument. The ICP-OES was calibrated using certified standards purchased from High Purity standards.

Example 1

Glacial acetic acid, water (5.0 wt. %), and the catalyst components in concentrations of 2400 ppmw Co, 90 ppmw Mn and 1750 ppmw Br were transferred to a 300 mL titanium autoclave equipped with a high pressure condenser, a baffle, an Isco pump and a cold trap after the condenser. The cobalt, manganese and ionic bromine were provided as cobalt (II) acetate tetrahydrate, manganese (II) acetate and aqueous hydrobromic acid, respectively. The autoclave was pressurized with approximately 50 psig of nitrogen and the homogeneous mixture was heated to the desired temperature of 160° C. in a closed system (i.e., with no gas flow) with stirring. At the given reaction temperature of 160° C., an air flow of 1500 sccm was introduced at the bottom of the solution and the reaction pressure was adjusted to the desired pressure of 180 psig. Para-xylene was fed to the mixture at a rate of 0.28 mL/min via a high pressure Isco pump (this is t=0 for the reaction time). After 30 seconds from the start of substrate feeding, 1.0 g of peracetic acid in 5.0 mL of acetic acid was introduced using a blow-case to start the reaction. The feed was stopped after 1 h and the reaction continued for an additional hour at the same conditions of air flow, temperature, and pressure. After the reaction time was completed, the air flow was stopped and the autoclave was cooled to room temperature and depressurized. The slurry was transferred to a beaker and heated to 85° C. and then vacuum filtered using a preheated fine frit without stirring. The mass of the filtrate was recorded. The solid was washed with 100 mL of 95% acetic acid, all at room temperature, four times without stirring. The solid was oven dried at 110° C. under vacuum overnight and then weighed.

The solid was then analyzed by liquid chromatography to analyze for the presence of 4-CBA. Cobalt, manganese and zirconium levels were analyzed by Thermo-ICP methods. The results are given in Table 2. The Off-gas was analyzed for CO and CO2 by ND-IR (ABB, Advanced Optima) and O2 by a paramagnetism detection system (Servomex, 1440 Model).

Examples 2 and 3

The experimental method in Example 1 was repeated twice with an addition of 25 ppmw zirconium. Zirconium acetate in acetic acid was used as the zirconium source. The results are given in Table 2.

Example 4

Glacial acetic acid, water (5.0 wt. %) and the catalyst components in concentrations of 2400 ppmw Co, 90 ppmw Mn and 1750 ppmw Br were transferred to a 300 mL titanium autoclave equipped with a high pressure condenser, a baffle, an Isco pump and a cold trap after the condenser. Cobalt, manganese and ionic bromine were provided as cobalt (II) acetate tetrahydrate, manganese (II) acetate and aqueous hydrobromic acid, respectively. The autoclave was pressurized with approximately 50 psig of nitrogen and the homogeneous mixture was heated to the desired temperature of 160° C. in a closed system (i.e., with no gas flow) with stirring. At the given reaction temperature of 160° C., an air flow of 1500 sccm was introduced at the bottom of the solution and the reaction pressure was adjusted to the desired pressure of 180 psig. Para-xylene was fed to the mixture at a rate of 0.28 mL/min via a high pressure Isco pump (this is t=0 for the reaction time). After 30 seconds from the start of substrate feeding, 1.0 g of peracetic acid in 5.0 mL of acetic acid was introduced using a blow-case to start the reaction. The feed was stopped after 1 h and the reaction continued for an additional hour at the same conditions of air flow, temperature, and pressure. The autoclave temperature was then raised to 205° C. and maintained at this temperature for 2 h with an air flow-rate at 1500 sccm and 180 psig pressure. After the reaction time was completed, the air flow was stopped and the autoclave was cooled to room temperature and depressurized. The slurry was transferred to a beaker and heated to 85° C. and then vacuum filtered using a preheated fine frit without stirring. The mass of the filtrate was recorded. The solid was washed with 100 mL 95% acetic acid, all at room temperature, four times without stirring. The solid was oven dried at 110° C. under vacuum overnight and then weighed.

The solid was then analyzed by liquid chromatography to analyze for the presence of 4-CBA. Cobalt, manganese and zirconium levels were analyzed by Thermo-ICP methods. The results are given in Table 2. The Off-gas was analyzed for CO and CO2 by ND-IR (ABB, Advanced Optima) and O2 by a paramagnetism detection system (Servomex, 1440 Model).

Examples 5 and 6

The experimental method of Example 4 was repeated twice with an addition of 25 ppmw zirconium. Zirconium acetate in acetic acid was used as the zirconium source. The results are given in Table 2.

Example 7

The experimental method of Example 4 was repeated with an additional 25 ppmw zirconium but with 1000 sscm of air flow during the 205° C. run time. The results are given in Table 2.

Example 8

Example 1 was repeated at 155° C. The results are given in Table 2.

Example 9

Example 1 was repeated with an addition of 25 ppmw zirconium at 155° C. Zirconium acetate in acetic acid was used as the zirconium source. The results are given in Table 2.

TABLE 2

Zr, Co, Mn and 4CBA levels in the solid TPA.

| Example | Conditions | Catalyst composition | Zr in the solid TPA (ppmw) | Co in the solid TPA (ppmw) | Mn in the solid TPA (ppmw) | 4CBA in the solid TPA (ppmw) |
|---|---|---|---|---|---|---|
| 1 | 180 psig, 160 C., 2 h | 2400 ppm (Co), 1750 ppm (Br), 90 ppm (Mn) | Not Applicable | 35 | <5 | 1543.5 |
| 2 | 180 psig, 160 C., 2 h | 2400 ppm (Co), 1750 ppm (Br), 90 ppm (Mn), 25 ppm (Zr) | 1.51 | 23 | <5 | 1360 |
| 3 | 180 psig, 160 C., 2 h | 2400 ppm (Co), 1750 ppm (Br), 90 ppm (Mn), 25 ppm (Zr) | 1.31 | 30 | <5 | 1254.2 |
| 4 | 180 psig, 160 C., 2 h. Then 205 C., 180 psig, 2 h. The same air-flow rate during digestion. | 2400 ppm (Co), 1750 ppm (Br), 90 ppm (Mn) | Not Applicable | 39 | <5 | 582.5 |
| 5 | 180 psig, 160 C., 2 h. Then 205 C., 180 psig, 2 h. The same air-flow rate. | 2400 ppm (Co), 1750 ppm (Br), 90 ppm (Mn), 25 ppm (Zr) | 1.6 | 41 | <5 | 431.1 |
| 6 | 180 psig, 160 C., 2 h. Then 205 C., 180 psig, 2 h. The same air-flow rate during digestion. | 2400 ppm (Co), 1750 ppm (Br), 90 ppm (Mn), 25 ppm (Zr) | 2.1 | 42 | <5 | 457.7 |
| 7 | 180 psig, 160 C., 2 h. Then 205 C., 180 psig, 2 h. Air-flow rate was reduced by ⅔ during digestion. | 2400 ppm (Co), 1750 ppm (Br), 90 ppm (Mn), 25 ppm (Zr) | 1.9 | 44 | <5 | 435.2 |
| 8 | 180 psig, 155 C., 2 h | 2400 ppm (Co), 1750 ppm (Br), 90 ppm (Mn) | Not Applicable | 52.9 | 1.8 | 3357 |
| 9 | 180 psig, 155 C., 2 h | 2400 ppm (Co), 1750 ppm (Br), 90 ppm (Mn), 25 ppm (Zr) | 1.7 | 16.1 | 0.7 | 1745 |

We claim:

1. A process for producing terephthalic acid, the process comprising combining in a reaction medium para-xylene, a solvent comprising water and a saturated organic add having from 2-4 carbon atoms, and an oxygen-containing gas, at a temperature from about 145° C. to about 175° C., in the presence of a catalyst composition comprising cobalt, manganese, zirconium, and bromine, wherein the zirconium is present in the reaction medium in an amount from about 1 ppm to 50 ppm and wherein the total amount of zirconium, nickel, chromium, and cerium is no more than 50 ppm, with respect to the weight of the liquid in the reaction medium.

2. The process according to claim 1, wherein the zirconium is present in the reaction medium in an amount from about 2 ppm to about 45 ppm.

3. The process according to claim 1, wherein the zirconium is present in the reaction medium in an amount from about 3 ppm to about 40 ppm.

4. The process according to claim 1, wherein the zirconium is present in the reaction medium in an amount from about 5 ppm to about 35 ppm.

5. The process according to claim 1, wherein the weight ratio of cobalt to manganese in the reaction mixture is from about 15 to about 250.

6. The process according to claim 1, wherein the saturated organic acid comprises acetic acid.

7. The process according to claim 1, wherein the temperature is from about 150° C. to about 170° C.

8. The process according to claim 1, wherein the temperature is from about 155° C. to about 165° C.

9. The process according to claim 1, wherein the zirconium is provided as one or more of: zirconium oxide, zirconium bromide, zirconium chloride, zirconium acetate, zirconium acetate hydroxide, zirconium acetylacetonate, zirconium hydroxide, zirconium butoxide, zirconium propoxide, or zirconyl acetate.

10. The process according to claim 1, wherein the zirconium is provided as zirconium acetate, zirconium acetate hydroxide, or zirconyl acetate.

11. The process according to claim 1, wherein the oxygen-containing gas comprises air.

12. The process according to claim 1, wherein the cobalt is provided in an amount from about 500 ppm to about 6,000 ppm, with respect to the Weight of liquid in the reaction medium.

13. The process according to claim 1, wherein the cobalt is provided in an amount from about 750 ppm to about 4,500 ppm, with respect to the weight of liquid in the reaction medium.

14. The process according to claim 1, wherein the cobalt is provided in an amount from about 1,000 ppm to about 4,000 ppm, with respect to the weight of liquid in the reaction medium.

15. The process according to claim 1, wherein the manganese is provided in an amount from about 20 ppm to about 425 ppm, with respect to the weight of liquid in the reaction medium.

16. The process according to claim 1, wherein the manganese is provided in an amount from about 20 ppm to about 300 ppm, with respect to the weight of liquid in the reaction medium.

17. The process according to claim 1, wherein the manganese is provided in an amount from about 20 ppm to about 200 ppm, with respect to the weight of liquid in the reaction medium.

18. The process according to claim 1, wherein the bromine is provided in an amount from about 750 ppm to about 6,000 ppm, with respect to the weight of liquid in the reaction medium.

19. The process according to claim 1, wherein the bromine is provided in an amount from about 900 ppm to about 5,000 ppm, with respect to the weight of liquid in the reaction medium.

20. The process according to claim 1, wherein the bromine is provided in an amount from about 1,000 ppm to about 4,500 ppm, with respect to the weight of liquid in the reaction medium.

21. The process according to claim 1, wherein the weight ratio of cobalt to bromine is from about 0.6 to about 10.

22. The process according to claim 1, wherein the weight ratio of cobalt to bromine is from about 0.7 to about 8.

23. The process according to claim 1, wherein the weight ratio of cobalt to bromine is from about 0.8 to about 5.

24. The process according to claim 1, wherein the process produces no more than about 1.2 moles COX per mole of para-xylene provided to the reaction medium.

* * * * *